United States Patent [19]

Campbell et al.

[11] 4,252,749
[45] Feb. 24, 1981

[54] PRODUCTION OF 1,2-DICHLOROETHANE WITH PURIFICATION OF DICHLOROETHANE RECYCLE

[75] Inventors: Ramsey G. Campbell, Berkeley; Wendell E. Knoshaug, Albany, both of Calif.

[73] Assignee: Stauffer Chemical Company, Westport, Conn.

[21] Appl. No.: 633,520

[22] Filed: Nov. 19, 1975

[51] Int. Cl.³ .............................................. C07C 17/02
[52] U.S. Cl. ...................................... 570/251; 570/262
[58] Field of Search ................................. 260/660, 656

[56] References Cited

U.S. PATENT DOCUMENTS

| | | | |
|---|---|---|---|
| 2,929,852 | 3/1960 | Benedict | 260/660 |
| 3,548,014 | 12/1970 | Jacobowski et al. | 260/652 P |
| 3,562,349 | 2/1971 | Pawloski et al. | 260/660 |
| 3,624,169 | 11/1971 | Fruhwirth et al. | 260/660 |
| 3,839,475 | 10/1974 | Kurtz et al. | 260/660 |
| 3,876,714 | 4/1975 | Coppens | 260/656 R |
| 3,920,761 | 11/1975 | Krome | 260/656 R |

FOREIGN PATENT DOCUMENTS

| | | | |
|---|---|---|---|
| 2427045 | 1/1975 | Fed. Rep. of Germany | 260/660 |
| 760308 | 10/1956 | United Kingdom | 260/660 |
| 1231127 | 5/1971 | United Kingdom | 260/660 |

Primary Examiner—Herbert Levine
Assistant Examiner—Joseph A. Boska
Attorney, Agent, or Firm—Joel G. Ackerman

[57] ABSTRACT

In a process for production of 1,2-dichloroethane by reaction of chlorine and ethylene at temperatures between about 85° C. and about 160° C. conducted in the presence of a liquid medium in which a recycle stream of 1,2-dichloroethane containing chloroprene and optionally other incompletely chlorinated $C_4$ hydrocarbons is introduced into the chlorination reaction system, the improvement comprising subjecting the recycle 1,2-dichloroethane to controlled chlorination by contacting it with a chlorination agent in such a manner and under such conditions as to partially chlorinate the chloroprene contained therein to produce a chlorinated derivative thereof, fractionating the thus treated 1,2-dichloroethane to separate chlorinated derivates of chloroprene therefrom, and introducing the thus purified 1,2-dichloroethane recycle into the chlorination reactor.

16 Claims, 2 Drawing Figures

4,252,749

PRODUCTION OF 1,2-DICHLOROETHANE WITH PURIFICATION OF DICHLOROETHANE RECYCLE

BACKGROUND AND PRIOR ART

This application relates to an improvement in a process for production of 1,2-dichloroethane by reaction of chlorine and ethylene in a liquid medium at temperatures between 85° and about 160° C. One process of this type is disclosed, for instance, in U.S. patent application No. 368,569 of Ramsey G. Campbell, filed June 11, 1973 and entitled "Process". A corresponding application has been published in Germany, Offenlegungsschrift 2,427,045, on Jan. 2, 1975. The disclosure of the said German patent application is hereby incorporated by reference into the present application.

Another process of this general type is disclosed in British Pat. No. 1,231,127 of Solvay et Cie.

In the process as described in German application No. 2,427,045 and the corresponding U.S. application, the liquid medium for the chlorination reaction comprises a liquid chlorinated hydrocarbon having two carbon atoms, or mixtures of two or more such compounds. Preferably, the liquid medium comprises 1,2-dichloroethane, 1,1,2-trichloroethane, or a mixture of these two compounds.

In one embodiment disclosed in the said German application, as well as in British Pat. No. 1,231,127, a stream of 1,2-dichloroethane recovered from the fractionation section of a process for pyrolysis of 1,2-dichloroethane to produce vinyl chloride, is introduced into the chlorination reaction system. In the process of the German application, the 1,2-dichloroethane is introduced as make-up for the circulating liquid medium. In addition, a fractionation column associated with the chlorination reactor serves to fractionate the 1,2-dichloroethane in the chlorination reactor, as well as such 1,2-dichloroethane as may be recycled from the pyrolysis process, or other sources, to remove impurities therefrom. The purified 1,2-dichloroethane from this fractionation column can be returned to the pyrolysis furnace.

The dichloroethane stream being recycled from the pyrolysis fractionation section to the chlorination reactor often contains minor but significant amounts of chloroprene and may also contain small amounts of other chlorinated C₄ hydrocarbons. For example, this stream may contain from 0.01 to about 0.3 mole percent chloroprene. This chloroprene can polymerize further in the process, particularly in the overhead of fractionation columns, resulting in plugging of the columns and/or associated lines.

The aforesaid German patent application discloses that this polymerization can be prevented by subjecting the recycle dichloroethane stream to a pre-chlorination step for chlorination of the chloroprene prior to introducing this recycle stream into the main chlorination reactor system. The chloroprene is converted to heavier boiling chlorinated compounds which will not polymerize and which are said to be separated either in the fractionation column associated with the main chlorination reactor (in the German application, in line 19, from the bottom of the fractionation column) or from the bottom of the chlorination reactor itself (in line 33).

British Pat. No. 1,266,676 of Knapsack A. G. discloses a process for removing products such as chloroprene from 1,2-dichloroethane in a combination process in which ethylene is first chlorinated to produce dichloroethane, the dichloroethane is cracked to produce vinyl chloride, and cracked dichloroethane can be recycled to the chlorination reactor. The chloroprene is removed from the dichloroethane (to prevent plugging up of equipment) by chlorinating it in the presence of ferric chloride to form a high boiler with respect to dichloroethane, and which can be readily separated from it. The patent discloses three methods of chlorinating the chloroprene: (a) introducing the dichloroethane containing chloroprene into the main chlorination reactor, in which the chloroprene will be chlorinated by chlorine and ferric chloride simultaneously with the chlorination of ethylene to produce dichloroethane; (b) chlorinating at least a portion of the overhead from the light ends column to convert the chloroprene to higher boiling compounds, and recycling the chlorinated overhead to the column, the higher boiling compounds being removed at the bottom and passed to a heavy ends column; and (c) chlorinating the overhead of the light ends column and recycling the chlorinated overhead to the column, with removal of dichloroethane as a sidestream from this column. The main chlorination reactor operates a temperature of about 50° C.

It has now been found that introduction of either chloroprene (as proposed in British Pat. No. 1,266,676) or chlorinated derivatives of chloroprene (as proposed in German application No. 2,427,045) into a chlorination reactor operating at a temperature of above 85° C., results in a loss of yield of 1,2-dichloroethane based on chlorine at temperatures above 85° C., and particularly between 85° and about 160° C. Surprisingly, in the main chlorination reactor, the chloroprene is not merely chlorinated to the next highest boiling derivative (mainly trichlorobutenes), but is further chlorinated to form higher boiling derivatives which may range up to fully chlorinated butane. Similarly, partially chlorinated derivatives of chloroprene are further chlorinated under these conditions to more highly chlorinated compounds. These more highly chlorinated compounds represent a yield loss of chlorine as they are removed from the chlorination reactor as heavy ends and disposed of as waste. The German patent application suggests that up to 3 moles of chlorine per mole of chloroprene may be used in the pre-chlorination step before introducing the recycled dichloroethane through the main chlorination reactor. The use of 3 moles of chlorine per mole of chloroprene represents an excessive use of chlorine in the process and, in addition, the more highly chlorinated compounds may be still further chlorinated in the main chlorination reactor, using up additional chlorine.

The introduction of the partially chlorinated recycle 1,2-dichloroethane into the fractionation column associated with the main chlorination reactor, rather than into the reactor itself, as suggested in the prior art, does not alleviate the situation. The partially chlorinated derivatives of chloroprene do not leave the column in the overhead or side streams; rather they pass downwards through the column, ultimately entering the chlorination reactor, and are further chlorinated.

It is an object of the present invention to provide an improved process for the removal of chloroprene from 1,2-dichloroethane which is being recycled to a reactor for chlorination of ethylene at a temperature of above 85° C.

A further object of the present invention is to provide a process for minimizing chlorine losses in a process of chlorinating ethylene utilizing chlorine in which 1,2-dichloroethane is to be recycled to the reactor.

Further objects and advantages of the invention will become apparent from the following description of the invention.

SUMMARY OF THE INVENTION

The invention herein comprises: In a process for production of 1,2-dichloroethane by reaction of ethylene with chlorine in a liquid medium at a temperature of between about 85° C. and about 160° C., and in which a stream of 1,2-dichloroethane containing a minor amount of chloroprene is introduced into the ethylene chlorination reaction zone, the improvement comprising (a) subjecting the stream of 1,2-dichloroethane to controlled chlorination by contacting it with a chlorination agent in such a manner and under such conditions as to partially chlorinate the chloroprene therein to produce a further chlorinated derivative thereof, (b) separating said further chlorinated derivative of chloroprene from the 1,2-dichloroethane, and (c) introducing the thus purified 1,2-dichloroethane stream from step (b) into the ethylene chlorination zone.

DETAILED DESCRIPTION OF THE INVENTION

As mentioned above, the invention herein can be utilized in any one of a number of processes for producing 1,2-dichloroethane from ethylene and chlorine at temperatures of above 85° C. For convenience, the invention will be described in terms of its utilization in connection with a process as disclosed in German application No. 2,427,045 and the entire disclosure of the said German patent application is incorporated herein by reference.

Figure 1:
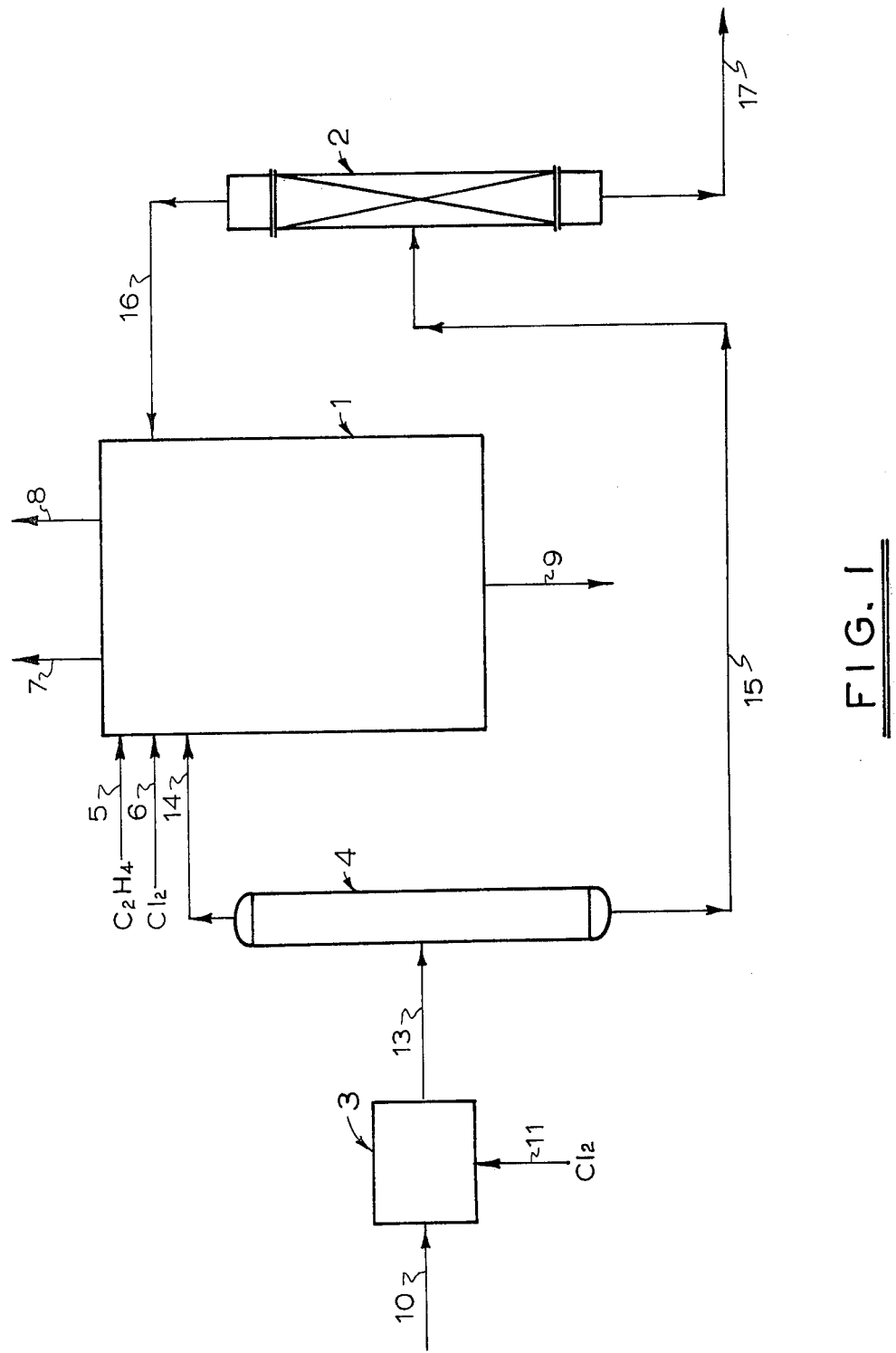
Figure 2:
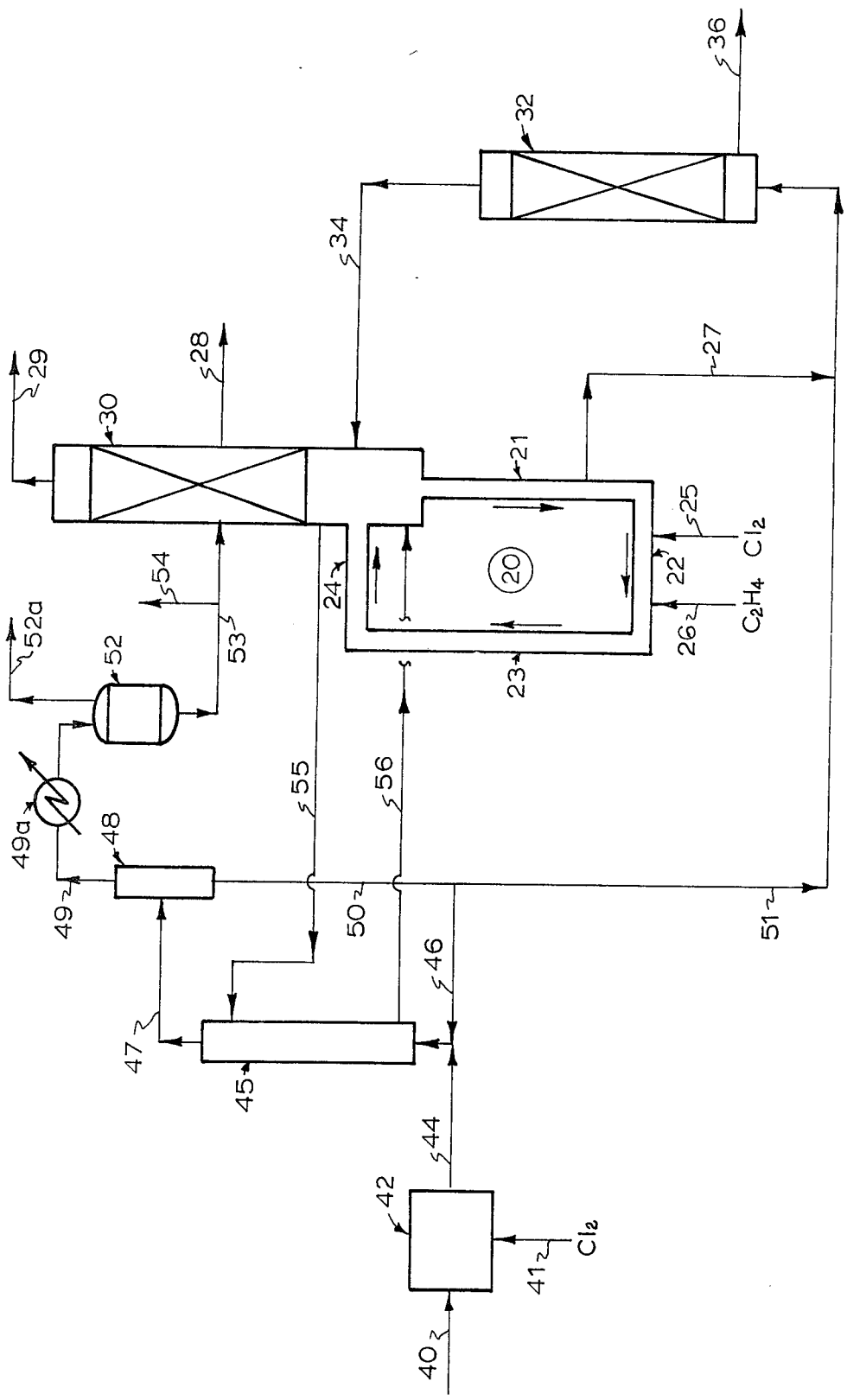

Reference is also made to the drawings in the present application, in which:

FIG. 1 represents the use of the invention in combination with a generalized process for chlorination of ethylene to produce 1,2-dichloroethane; and FIG. 2 represents a more detailed embodiment of the invention in combination with a process as described in the said German application.

Referring to the general flow scheme of FIG. 1, ethylene in line 5 and chlorine in line 6 are introduced into a chlorination zone 1, which generally comprises a chlorination reactor, and which may be one of the various types as are known in the art, together with such associated fractionation equipment as may be necessary to separate the products of this reactor into one or more fractions. At least three main fractions are recovered from the chlorination zone: a 1,2-dichloroethane fraction (stream 7) a light ends fraction, comprising primarily components boiling below 1,2-dichloroethane (stream 8) and a heavy ends fraction comprising primarily components boiling above 1,2-dichloroethane (stream 9). In general, the chlorination reactor will operate at a temperature of about 85° to about 160° C., preferably about 85° to about 140° C., and most preferably about 85° to about 120° C. As heretofore mentioned, the liquid in which the chlorination reaction is conducted is composed primarily of one or more $C_2$ chlorinated hydrocarbons, preferably 1,2-dichloroethane, 1,1,2-trichloroethane or mixtures thereof. Some of the liquid medium will be removed along with the product 1,2-dichloroethane in the fractionation section associated with the chlorination reactor.

If the chlorination reactor, for example, is located in a plant producing vinyl chloride by pyrolysis of 1,2-dichloroethane, it may be considered advantageous to recycle part or all of the unpyrolyzed dichloroethane to the chlorination section for fractionation and purification in the fractionating column or columns associated with the chlorination reactor. This stream of uncracked 1,2-dichloroethane will often contain minor amounts of chloroprene, generally from 0.1 to about 0.3 mole percent and may also contain as impurities minor amounts of other incompletely chlorinated $C_4$ hydrocarbons such as 1,4-dichlorobutene-2. As mentioned previously, it has been found that introduction of chloroprene and/or other incompletely chlorinated $C_4$ hydrocarbons (e.g. partially chlorinated derivatives of chloroprene) into a chlorination zone operating at a temperature of above 85° C. results in a use of excess amounts of chlorine in producing highly chlorinated $C_4$ hydrocarbons which, in any case, must be disposed of as waste. Similarly, chlorinating the chloroprene in a pre-chlorination step as suggested in German patent application No. 2,427,045 would also result in additional chlorine being utilized to produce waste products if the products of this pre-chlorination step were introduced into the main chlorination reaction zone.

According to the invention, the unpyrolyzed 1,2-dichloroethane stream in line 10 is contacted with a chlorinating agent in such a manner as hereinafter described to convert the chloroprene by partial chlorination to compounds which are high boilers with respect to 1,2-dichloroethane.

The partial chlorination may be performed according to any of the methods known in the art for this purpose as long as the method employed does not significantly affect the desired components in the stream or introduce other undesirable impurities. The preferred chlorinating agent is chlorine, which may be introduced in either the liquid or gaseous state. Other chlorinating agents for chlorinating chloroprene may be used, such as aluminum chloride. In addition to chloroprene, other $C_4$ chlorinated hydrocarbons present as impurities in the 1,2-dichloroethane may also be further chlorinated in this step.

In general, the partial chlorination will be conducted at temperatures of between 0° C. and 100° C., preferably between 20° C. and 60° C. At temperatures much over 100° C., selectivity of the chlorination may be lessened, and some 1,2-dichloroethane may become further chlorinated. If chlorine is employed as the chlorinating agent, the chlorination may be conducted either with or without any of the known chlorination catalysts, such as ferric chloride. The amount of chlorine used is between about 0.5 and about 2, preferably between about 0.85 and about 1.75, moles of chlorine per mole of chloroprene. Most preferred is an amount of about 0.95–1.3 moles of chlorine per mole of chloroprene. The reaction is generally conducted at ambient pressure; however the pressure may be varied if desirable.

Though the detailed description of the invention which follows is phrased in terms of partial chlorination of chloroprene with chlorine, as discussed previously other chlorination agents can be utilized in a generally similar manner.

The partial chlorination may be carried out in a separate pre-chlorination zone 3, or may be carried out by simply introducing chlorine or another chlorinating agent into the 1,2-dichloroethane line 10 without any special apparatus. The 1,2-dichloroethane, now containing chlorinated derivatives of chloroprene and other C₄ compounds (if present) is passed in line 13 into a distillation apparatus 4, which may be a single plate evaporator. In apparatus 4, 1,2-dichloroethane is readily separated from chlorinated derivatives of chloroprene; 1,2-dichloroethane is removed as overhead from the column and conveyed into the main chlorination reactor 1, via line 14. The chlorinated derivatives of chloroprene (and other C₄ compounds if present) are removed as a bottoms product from apparatus 4 in line 15, and preferably are combined with the heavy ends fraction from the chlorination zone 1, in line 9, and the combined products passed through a heavy ends/tar still 2 in which 1,2-dichloroethane is removed and returned to the chlorination reactor in line 16. Heavy ends, including chlorinated derivatives of chloroprene, are removed from the tar still in line 17 and passed to waste disposal or recovery.

Referring now to FIG. 2, the chlorination reactor 20 is preferably composed of a circulating loop reactor having a down leg 21, up leg 23, and cross-over legs 22 and 24. Chlorination reactor 20 is generally shown schematically as being similar to FIG. 2 of German application No. 2,427,045; however, any of the constructions disclosed in that application and any equivalent constructions known in the art may be utilized. Chlorine in line 25 and ethylene in line 26 are introduced into the reactor at appropriate points. The reactor 20 contains a circulating liquid medium which may be 1,2-dichloroethane, 1,1,2-trichloroethane, or mixtures thereof, and containing an appropriate catalyst, for example, ferric chloride. As disclosed in the said German patent application, there is preferably a slight excess of ethylene over and above the amount required to react with the chlorine; however, chlorine may be present in a small excess. Temperatures of the chlorination reactor are those at which the circulating liquid medium does not vaporize in the reaction zone under the conditions employed. In general, the temperature is maintained at between about 85° C. and about 180° C., preferably 85° C. to about 160° C., under sufficient system pressure so that the 1,2-dichloroethane liquid medium (which normally boils at about 83.5° C.) will not vaporize in the reaction zone 20. The pessures employed may vary considerably provided they are sufficient to prevent vaporization of the 1,2-dichloroethane at the temperature of the reaction zone.

Associated with the chlorination reactor 20 is fractionation or distillation column 30 which is used to fractionate the products of the chlorination reaction as well as other substances as discussed below. A pressure differential is maintained between the chlorination zone 20 and the fractionation column 30 such that at the temperatures employed, the heat of reaction of the chlorination of ethylene is utilized to vaporize a portion of the circulating liquid medium in the fractionation zone in order to conduct a fractionation of the liquid medium, reaction products and unreacted starting materials. The fractionation zone produces a light ends fraction 29 as overhead. The light ends fraction in line 29 can be sent to further fractionation (not shown) to recover 1,2-dichloroethane and light hydrocarbons. A side stream 28 is withdrawn, comprising 1,2-dichloroethane product of the chlorination reaction, which, in a plant for production of vinyl chloride, is most advantageously conveyed to the cracking step to be pyrolyzed. Heavy ends, that is, components boiling higher than 1,2-dichloroethane, are returned from the bottom of the fractionation column into the chlorination reactor and eventually removed from this reactor in line 27.

A stream of 1,2-dichloroethane, recovered from the fractionation section of a pyrolysis unit, which may be in the same plant or in another plant, and containing minor amounts of chloroprene and possibly other incompletely chlorinated C₄ hydrocarbons enters the system in line 40 and is contacted with chlorine (or another chlorination agent) introduced in line 41. As in FIG. 1, the chlorine may be mixed with the dichloroethane in a pre-chlorination zone 42, or the chlorine may simply be introduced into line 40 and mixed with the dichloroethane in the line. The dichloroethane stream, after contact with the chlorine, is passed through line 44, preferably mixed with recycle in line 46 and introduced into distillation apparatus 45. Apparatus 45 may be a single-plate evaporator or may be a more complicated system. The products leave apparatus 45 in overhead line 47 and are separated in a knock-out drum 48 into liquid and gaseous products. The gaseous products comprise substantially purified 1,2-dichloroethane containing little or no chloroprene or chlorinated derivatives thereof. This gaseous product is conveyed through line 49 into a condenser 49a and then into a liquid-gas separator 52, which is operated at atmospheric pressure, with gaseous products vented through line 52a, and the liquid product, containing primarily 1,2-dichloroethane, is introduced into fractionation column 30 through line 53. If desired, a portion of this dichloroethane may be taken off in line 54 and combined with the dichloroethane product of the column in line 28, and the combined dichloroethane streams forwarded to the pyrolysis unit. The liquid product from knockout drum 48 is removed in line 50, a portion of it returned to distillation apparatus 45 in line 46, and the remainder passed through line 51, preferably combined with heavy ends from the chlorination reactor in line 27, and introduced into tar still 32. 1,2-dichloroethane contained in streams 27 and 51 is removed by distillation of the combined heavy ends stream. This dichloroethane is returned to the chlorination zone in line 34. Heavy ends are removed from the tar still in line 36 and passed to waste disposal or for further processing.

In one embodiment, the heat utilized to conduct the separation in distillation apparatus 45 is supplied by reaction heat from the chlorination reactor 20. This is most advantageously performed by heat exchange with a vapor drawn off from the top of the chlorination reactor in line 55, introduced in indirect heat exchange with the combined feeds to the distillation column 45, recovered as a liquid and returned in line 56 to the chlorination reactor. Alternatively, the heat for operation of the distillation column 45 can be wholly or partly supplied by steam or any other high temperature gas which is cooled or condensed in indirect heat exchange with the products being distilled in the column.

The heavy ends removed in lines 50 and 51 comprise chlorinated derivatives of chloroprene and/or such other C₄ hydrocarbons as may be present, together with 1,2-dichloroethane. About 95% of the chloroprene and such other chlorinated hydrocarbons as may be originally present in the dichloroethane stream in line 40 are removed by the combination of partial chlorination and distillation. The vapor products from distillation apparatus 45 in line 49 comprise between about 90 and about 98% of the stream introduced in line 40; thus the stream in line 51 containing chlorinated derivatives of chloroprene and similar compounds comprises about 2 to 10% of the original 1,2-dichloroethane stream in line 40.

As is known in the art, processes conducted similar to FIGS. 1 and 2 will utilize pumps, compressors, heat exchangers and similar apparatus which are not shown in these diagrams.

The following examples present comparative data on the operation of a process as described in FIG. 2 and as described in the German patent application.

EXAMPLE 1 (PRIOR ART)

This example shows the operation of the process as shown in FIG. 1 of German patent application No. 2,427,045, in which the recycle dichloroethane in line 40 is contacted with chlorine, and the products are introduced into the chlorination reactor 20.

Recycle 1,2-dichloroethane containing 2700 ppm chloroprene was partially chlorinated using 1.10 moles of chlorine per mole of chloroprene (0.0246 lb chlorine/gallon of dichloroethane). The reaction was carried out at ambient temperature (20° C.) by circulating the dichloroethane by means of a pump and injecting the chlorine as a gas into the pump discharge. At the completion of the chlorine addition, the chloroprene concentration was less than 10 ppm.

The partially chlorinated recycle dichloroethane was fed to the distillation column 30 of the chlorinator 20 at a rate of 20 gallons/hour. The chlorinator was operated at the following conditions:

$C_2H_4$ Feed rate—534 g moles/hr
$C_2H_4/Cl_2$ Feed Ratio—1.05
% Oxygen in Chlorine—1.0%
Pressure at Top of Reactor—11 PSIG
Reaction Temperature—111° C. Maximum The hydrogen chloride generation rate was 19 g moles/hour. Material balances over the chlorinator gave the following results:

moles of 1,2-dichloroethane produced/mole of chlorine fed=0.958 of the ethylene reacted, 99.1% was converted to 1,2-dichloroethane Thus, the yield of 1,2-dichloroethane was 95.8%, based on total chlorine feed (to both the partial chlorinator and the main chlorinator).

EXAMPLE 2

This Example shows results obtained utilizing the process of the present invention, in which the partial chlorination of the chloroprene is carried out with chlorine, and the chlorinated derivatives of chloroprene are separated from the 1,2-dichloroethane prior to its introduction into the chlorination reactor 20.

Recycle 1,2-dichloroethane was partially chlorinated using the procedure outlined in Example 1. The recycle originally contained 1130 ppm chloroprene. By reaction with 1.10 moles of chlorine/mole of chloroprene (0.0103 lb. chlorine/gallon of dichloroethane), the chloroprene content was reduced to less than 10 ppm.

The partially chlorinated recycle dichloroethane was fed to a single plate distillation unit operating at atmospheric pressure and a pot temperature of 85° C. Of the feed to the unit, 95% was taken off as a distilled product and 5% was removed as a heavy ends stream. The distilled product was condensed and collected and fed to the chlorinator 20 as described in Example 1. The chlorinator was operated as described in Example 1. The hydrogen chloride generation rate was 5 g moles/hour. Material balances gave the following results:

moles of EDC produced/mole of chlorine fed=0.986 of the ethylene reacted, 99.2% was converted to 1,2-dichloroethane Thus, the yield of 1,2-dichloroethane was 98.6% based on total chlorine fed 1 to both the partial chlorinator and the main chlorinator.

Operation utilizing the principle of the present invention, in a typical plant producing about 1 billion pounds of vinyl chloride per year, will result in a saving of chlorine of about 17.5 million pounds per year.

What is claimed is:

1. In a process for production of 1,2-dichloroethane by chlorination of ethylene with chlorine in a liquid medium comprising 1,2-dichloroethane at a temperature of between about 85° C. and about 160° C., and in which a stream of 1,2-dichloroethane containing a minor amount of chloroprene as an impurity is available for introduction into the ethylene chlorination reaction zone, the improvement whereby introduction of chloroprene and/or chlorinated derivatives thereof into the ethylene chlorination reaction zone is avoided, comprising:

(a) Subjecting the stream of 1,2-dichloroethane to a controlled pre-chlorination by contacting it with a chlorination agent in such manner and under such conditions as to partially chlorinate the chloroprene therein to produce one or more further chlorinated derivatives thereof;

(b) separating said further chlorinated derivatives of chloroprene from the 1,2-dichloroethane; and (c) introducing the 1,2-dichloroethane substantially free of chloroprene or chlorinated derivatives thereof into the ethylene chlorination reaction zone.

2. A process according to claim 1 in which the chlorination agent is chlorine.

3. A process according to claim 2 in which the chlorine utilized in step (a) is introduced in an amount of between about 0.5 and 2 moles of chlorine per mole of chloroprene.

4. A process according to claim 2 in which the amount of chlorine introduced into step (a) is from about 0.85 to about 1.5 moles of chlorine per mole of chloroprene.

5. A process according to claim 2 in which the amount of chlorine introduced into step (a) is between about 0.95 and about 1.3 moles of chlorine per mole of chloroprene.

6. A process according to claim 2 in which the chlorine is introduced into step (a) in the form of gas.

7. A process according to claim 2 in which the chlorine introduced into step (a) in the form of liquid.

8. A process according to claim 1 in which the stream of 1,2-dichloroethane further contains a minor amount of an incompletely chlorinated $C_4$ hydrocarbon other than chloroprene.

9. A process according to claim 1 in which vapor generated in the ethylene chlorination zone is utilized to furnish heat for the conduct of step (b), the vapor being thereby condensed, and the condensed vapor recycled to the ethylene chlorination zone.

10. A process according to claim 1 in which heat for the conduct of step (b) is supplied by indirect heat exchange with steam.

11. A process according to claim 1 in which the ethylene chlorination reaction is conducted at a temperature between about 85° C. and about 140° C.

12. A process according to claim 1 in which the ethylene chlorination reaction is conducted at a temperature between about 85° C. and about 120° C.

13. A process according to claim 1 in which step (a) is conducted at a temperature of between about 0° C. and about 100° C.

14. A process according to claim 1 in which step (a) is conducted at a temperature of between about 20° C. and about 60° C.

15. A process according to claim 1 in which the chlorination agent comprises chlorine and a chlorination catalyst.

16. A process according to claim 1 in which the liquid medium is continuously circulated through the ethylene chlorination zone and said reaction zone is operated at a temperature and pressure such that the circulating liquid medium is maintained at a temperature below its boiling point in this zone.

* * * * *